United States Patent [19]

Akimoto

[11] Patent Number: 4,739,521
[45] Date of Patent: Apr. 19, 1988

[54] MEDICAL IMAGE DIAGNOSTIC SYSTEM
[75] Inventor: Taizo Akimoto, Kanagawa, Japan
[73] Assignee: Fuji Photo Film Co., Ltd., Kanagawa, Japan
[21] Appl. No.: 838,863
[22] Filed: Mar. 12, 1986

[30] Foreign Application Priority Data

Mar. 12, 1985 [JP] Japan ................... 60-47384

[51] Int. Cl.$^4$ ............................................. H04B 9/00
[52] U.S. Cl. ................................ 455/612; 354/131;
358/244; 455/617
[58] Field of Search ............... 455/610, 612, 617;
358/112, 244; 128/712; 378/98, 99, 100;
354/131

[56] References Cited

U.S. PATENT DOCUMENTS

| | | | |
|---|---|---|---|
| 4,359,759 | 11/1982 | McBride et al. | 378/99 |
| 4,413,630 | 11/1983 | Anderson et al. | 128/712 |
| 4,473,841 | 9/1984 | Murakoshi et al. | 455/612 |
| 4,519,250 | 5/1985 | Sumino | 455/612 |
| 4,566,767 | 1/1986 | Akisada et al. | 354/76 |
| 4,592,633 | 6/1986 | Seki et al. | 354/76 |

FOREIGN PATENT DOCUMENTS

| | | |
|---|---|---|
| 59-182429 | 10/1984 | Japan. |
| 60-118828 | 6/1985 | Japan. |
| 61-77827 | 4/1986 | Japan. |
| 61-77828 | 4/1986 | Japan. |
| 61-77829 | 4/1986 | Japan. |
| 61-77830 | 4/1986 | Japan. |
| 61-61526 | 4/1986 | Japan. |
| 61-61527 | 4/1986 | Japan. |
| 61-173232 | 8/1986 | Japan. |

OTHER PUBLICATIONS

Bock—The KCA 100—vol. 10—No. 167—Sep. 1979—International Broadcast Engineer (Great Britain), pp. 18-20, 22.

*Primary Examiner*—Joseph A. Orsino, Jr.
*Attorney, Agent, or Firm*—Sughrue, Mion, Zinn, Macpeak, and Seas

[57] ABSTRACT

A medical image diagnostic system including a diagnostic image detecting device, an image processing device receiving the output of the diagnostic image detecting device, a video signal converting circuit receiving the output of the image processing device, an electro-optic converting circuit receiving the output of the video signal converting circuit, an opto-electric converting circuit coupled to the electro-optic converting circuit via an optical cable, and an image display device driven in response to the output of the electro-optic converting circuit. Further, there may be provided a device for photographing the images displayed by the image display device. The photographing device may be remotely controlled.

13 Claims, 4 Drawing Sheets

MEDICAL IMAGE DIAGNOSTIC SYSTEM

BACKGROUND OF THE INVENTION

The present invention generally relates to a medical image diagnostic system and more particularly to a medical picture diagnosis system provided with an image processing device, an image display device for displaying an image formed by the image processing device, and a photographing device for photographing and recording the images thus displayed in a desired format.

Recently, in the field of medical diagnostic systems, there has been known a system including a device for processing an image signal transferred from a computer tomography apparatus (X-ray CT) or a nuclear magnetic resonance computer tomography apparatus (NMRCT) using a computer to thereby obtain a clear image of a portion of the patient's body. The system further includes a device responsive to the image-processing device for displaying the image on a display device, for example, a cathode-ray tube (CRT) display device, and a device for photographing the displayed image.

For example, a CT system using X-rays has been put to widespread use because such a system provides superior image quality since slight differences in X-ray absorption coefficients can be readily recognized. Further, besides such systems using X-rays, there have been known an emission CT device using radioisotopes in which the distribution of radioisotopes absorbed in a patient's body is scanned by a detector so as to reconstruct a tomographic image of the body, a positron CT system wherein X-ray beams opposed to each other by 180 degrees are generated when protons are combined with electrons and extinguished, and an NMRCT system which utilizes nuclear magnetic resonance (which has the advantage of no radiation hazard) and which is particularly suitable for detecting the state of fluids in the patient's body.

Moreover, there has been known a camera system, referred to as a medical imaging camera, in which an image displayed on a display device such as a CRT can be photographed in a desired format. This camera system is suitable for recording and preserving images displayed on a display device in accordance with a signal transferred from a diagnostic system. In this system, the exposed film is developed by an automatic developer.

Of these two types of systems, one is a medical diagnostic system for displaying a preferred diagnostic image of an affected part of a patient's body, and the other is a system for recording the displayed image. Recently, attempts have been made to combine these two types of systems into one so as to obtain a complete medical image diagnostic system. Such a medical image diagnostic system can be easily constructed merely by connecting the output signal of a diagnostic image detection device to a video input terminal of an image display device through an appropriate image processing device and a video signal converting circuit.

In such a medical image diagnostic system, there occurs no difficulty in the case where the diagnostic image detection device, the image display device, and the displayed image photographing device are connected with each other using ordinary high-frequency cables if all these devices are arranged integrally with each other or disposed close to each other. However, in the case where the image display device and the displayed image photographing device are located at some distance from one another, problems in signal transmission often occur.

Further, there is a need for the image density to be made greater, for example, by increasing the number of scanning lines from about 500 to about 1000. In such a case, a sufficient bandwidth cannot be obtained using ordinary high-frequency cables. Moreover, the phase characteristics of the image signal are such that, in the case where the video converting circuit, the image display device, and the displayed image photographing device are connected to each other through ordinary high-frequency cables of a length of several tens of meters or more, the image signal transferred from the video converting circuit cannot be correctly displayed on the display device, and in some cases, the displayed image cannot be clearly reproduced by the displayed image photographing device.

SUMMARY OF THE INVENTION

The present invention has been attained in view of the foregoing disadvantages, and an object of the present invention is to provide a medical image diagnostic system comprising image output means, an image display device and displayed image photographing means, the image output means being constituted of a diagnostic image detecting means, image processing means, and a video signal converting circuit. The system is arranged such that an image obtained from the image output means is transferred to the image display device without distortion, and the displayed image an be photographed and recorded using the displayed image photographing means even when the image output means, the image display device, and the displayed image photographing means are disposed separately from each other and located a relatively long distance apart from one another.

More particularly, in order to attain the above-mentioned objects, the medical image diagnostic system according to the present invention is constituted of a diagnostic image detecting means, image processing means, a video signal converting circuit, an electro-optic converting circuit, an optical fiber cable, an optoelectric converting circuit, and an image display device. Displayed image photographing means may additionally be provided.

In the system according to the present invention, preferably, the electro-optic converting circuit is arranged to directly perform amplitude modulation of an analog video signal.

In the system according to the present invention, preferably, the photography control means for controlling the photographing means is connected to remote operation means for remotely operating the photography control means through an internal conductive metal member of a opto-metallic composite cable constituted of an optical fiber and a metal cable. In this manner, one can remotely control the photography control means so as to ON-OFF control the power source of the photographing means and the of the optoelectric signal converting circuit, or set the photographic conditions, such as the magnification factor or photographic format, exposure operations, etc. Although these control operations may be performed using a conductive element of an opto-metallic composite cable, the opto-metallic composite cable may be arranged such that a plurality of optical fiber units are internally provided and the electro-optic converting circuit and the opto-electric converting circuit are connected through one of the optical fiber units, whereby a digital signal from the remote operation means is transmitted to the photography control means to perform the setting of the photographing conditions. Thus, other ones of the plurality of optical fiber units may be used for transmitting a signal representing the status of the photographing conditions as set and the start of photography to the status indication device. For example, the existence of film is detected by detecting means so as to produce a signal representing the ready state.

A remote operation means and photographing control means of the type described above are disclosed in detail, for example, in Japanese Patent Application Nos. 58-57048 and 58-226218, Japanese Utility Model Application No. 59-145165, Japanese Patent Application Nos. 59-201283, 59-201284, and 60-13447.

DESCRIPTION OF THE PREFERRED EMBODIMENTS

Figure 1:
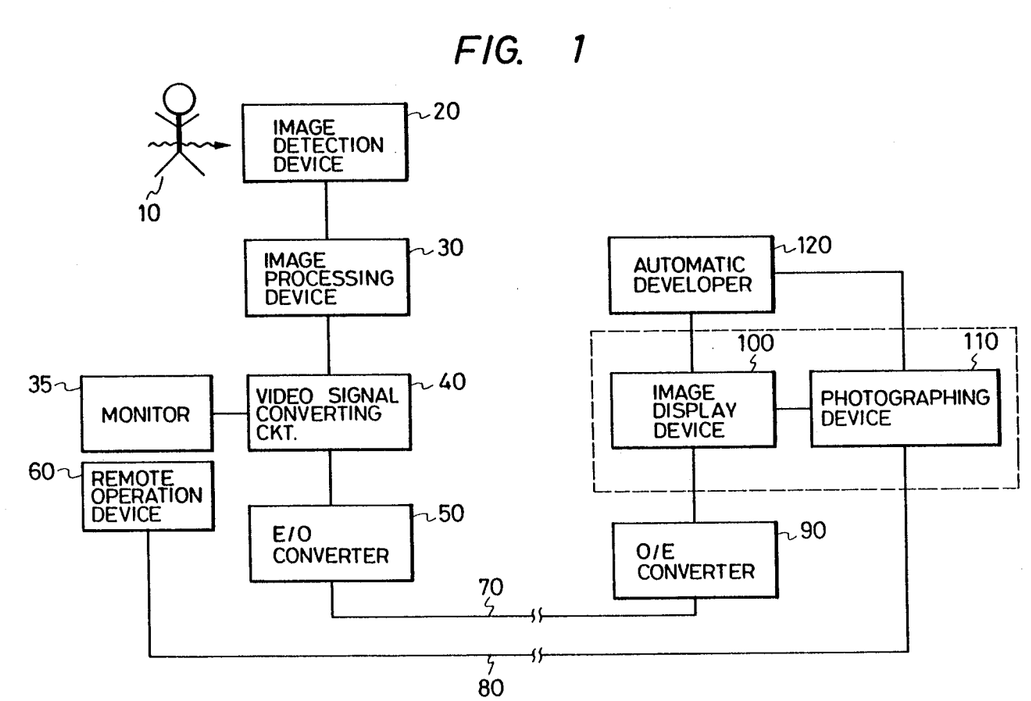
FIG. 1 is a schematic block diagram of a preferred embodiment of a medical image diagnostic system according to the present invention.

FIG. 1 is a schematic block diagram showing a system according to the present invention.

In FIG. 1, reference numeral 20 designates a diagnostic image detection device for detecting response information from a patient 10. As the device 20, it is possible to use known devices, for example, the scintillator and photomultiplier of an X-ray CT system, a the probe head of an NMR-CT system, or the image intensifier of an X-ray system.

The output of the diagnostic image detection device 20 is transferred to an image processing device 30 in which image processing such as image reconstruction, gradation conversion, frequency enhancement, addition/subtraction, and the like are performed by a computer. The output of the device 30 is applied to a video signal converting circuit 40 and is converted thereby into a video signal, which is in turn transferred to an electro-optic signal converting circuit (hereinafter referred to as an E/O converter) 50 and is, at the same time, displayed on a monitor 35 of a console of the diagnostic system. The E/O converter 50 is connected to an opto-electric signal converting circuit (hereinafter referred to an O/E converter) 90, the output of which is applied to a video input terminal of an image display device 100. The display device 100 is integrally provided with a displayed image photographing device 110 so that it is possible to display the received video signal and at the same time to photograph the displayed image. The film on which displayed images have been photographed is developed by an automatic developer 120. Further, a remote operation device 60 for remotely operating the displayed image photographing device 110 is provided in the console of the diagnostic system at the display device 35. Wiring 80 for the remote operation device 60 is provided parallel to an optical fiber cable 70. Further, it is possible to simplify the wiring 80 by using the conductive metal member of the optical fiber cable 70 if the cable is an opto-metallic composite cable.

An arrangement in which an image display device 100 and a displayed image photographing device 110 are integrated with each other is disclosed in detail in Japanese Patent Application Nos. 59-201283, 59-201287, 59-201284, and 59-201286, Japanese Utility Model Application Nos. 59-145164 and 59-145165, all of which have been filed by the present applicant.

Figure 2:
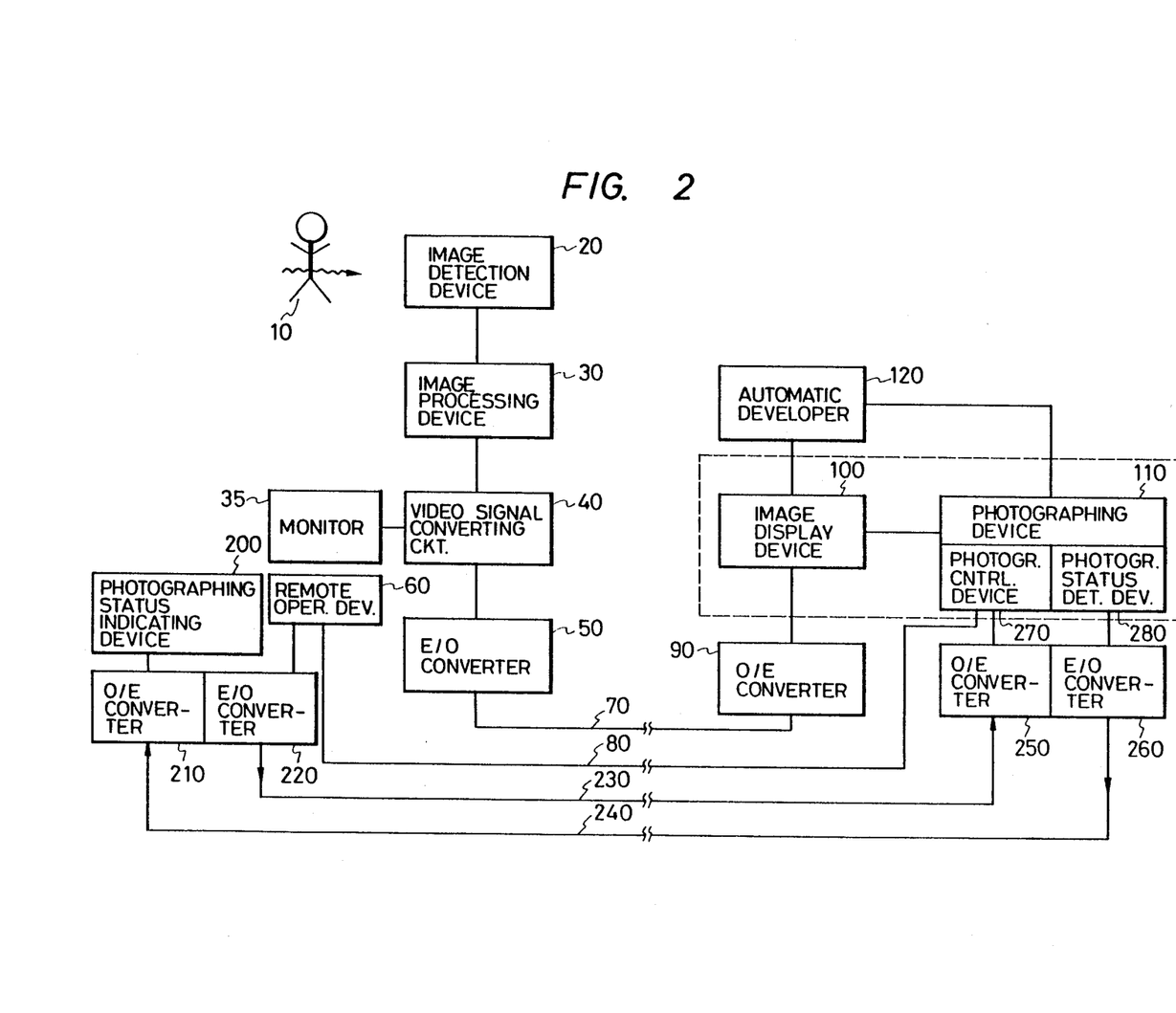
FIG. 2 is a schematic block diagram of another embodiment of the system according to the present invention.

FIG. 2 shows a modification of FIG. 1, and in FIG. 2, elements corresponding to those in FIG. 1 are correspondingly referenced.

On an operation panel of the remote operation device 60 there are provided various switches, such as power source ON-OFF switches, for a photography control device 270, an analog video signal O/E converter 90, digital signal O/E converters 210 and 250, digital signal E/O converters 220 and 260, etc., (which will be described in detail below with reference to FIG. 3). The remote operation device 60 is connected to a displayed image photographing device 110 through a transmission cable 80.

The displayed image photographing device 110 is provided with a photography control device 270 and photograph status detecting device 280, and is arranged to energize driving motors or the like in response to a switching operation of the remote operation device 60 so as to move an actuating member to a position determined on the basis of the operation of a microcomputer (which will be described below with reference to FIG. 3) provided in the displayed image photographing device 110. When the actuating member is thus located in a suitable position, this position is detected by a position detection device provided in association with the actuating member, and the thus-detected status of the position is indicated by a photography status indication device 200 through a transmission cable 240.

As the transmission cable 240, although a high-frequency cable or a metal member may be used in the case where the transmission distance is short, it is preferable to use an optical cable in order to maintain signal characteristics and to make it possible to employ long distance transmission. Therefore, in FIG. 2, an output signal from the remote operation device 60 is subjected to electro-optic signal conversion by the E/O converter 220 and then applied to the optical cable 230. At the side of the displayed image photographing device 110, the received optical signal is subjected to opto-electric signal conversion by the O/E converter 250 and then applied to the photography control device 270. Similarly, the output signal of photography status detection device 280 is subjected to electro-optic signal conversion by the E/O converter 260 and then applied to the optical cable 240, and at the side of the remote operation device 60, the transferred optical signal is subjected to opto-electric signal conversion by the O/E converter 210 and indicated by the photography status indication device 200.

Further, since the E/O converters 220 and 260 and the O/E converters 210 and 250 process digital signals, each of the E/O converters can be constituted of a level converting circuit, a light-emitting device (for example an LED), and a light-emitting device driving circuit which drives the light-emitting device when a signal which satisfies predetermined interface conditions is applied to the level converting circuit. On the other hand, the O/E converter can be constituted of a light-detecting element (for example, a photo diode), an amplifier, a comparator, and a level converting circuit. Light entering the O/E converter through an optical fiber is converted into a current signal by the photo diode or the like, amplified using the amplifier, compared by the comparator, and converted to have a level satisfying predetermined interface conditions.

The signal applied from the remote operation device 60 to the digital signal E/O converter 220, as well as the signal applied from the photography status detection detector 280 of the displayed image photographing device 110 to the digital signal E/O converter 260, are digital multiplex signals multiplexed using a known signal multiplexing method. Therefore, in the digital signal E/O converters 220 and 260, only in the case where predetermined interface conditions are satisfied is the relationship between the input electric signal and output optical signal determined such that "1" indicates that the converter is ON and "0" indicates that it is OFF. Similarly, the signal applied from the digital signal O/E converter 250 to the photography control device 270 and the signal applied from the digital signal O/E converter 210 to the photography status indication device 200 are demodulated using a known digital multiplex signal demodulating method.

The digital signal E/O converter is a readily obtainable commercial item, and in the case of a single unidirectional device, it is possible to use, for example, an OMLINK Z3K-T16P8E and OMLINK Z3K-R16P8E made by OMRON TATEISHI ELECTRONICS COMPANY, while in the case of a single bidirectional device, it is possible to use, for example, an OMLINK Z3K-M16P8B made by the same company.

Figure 3:
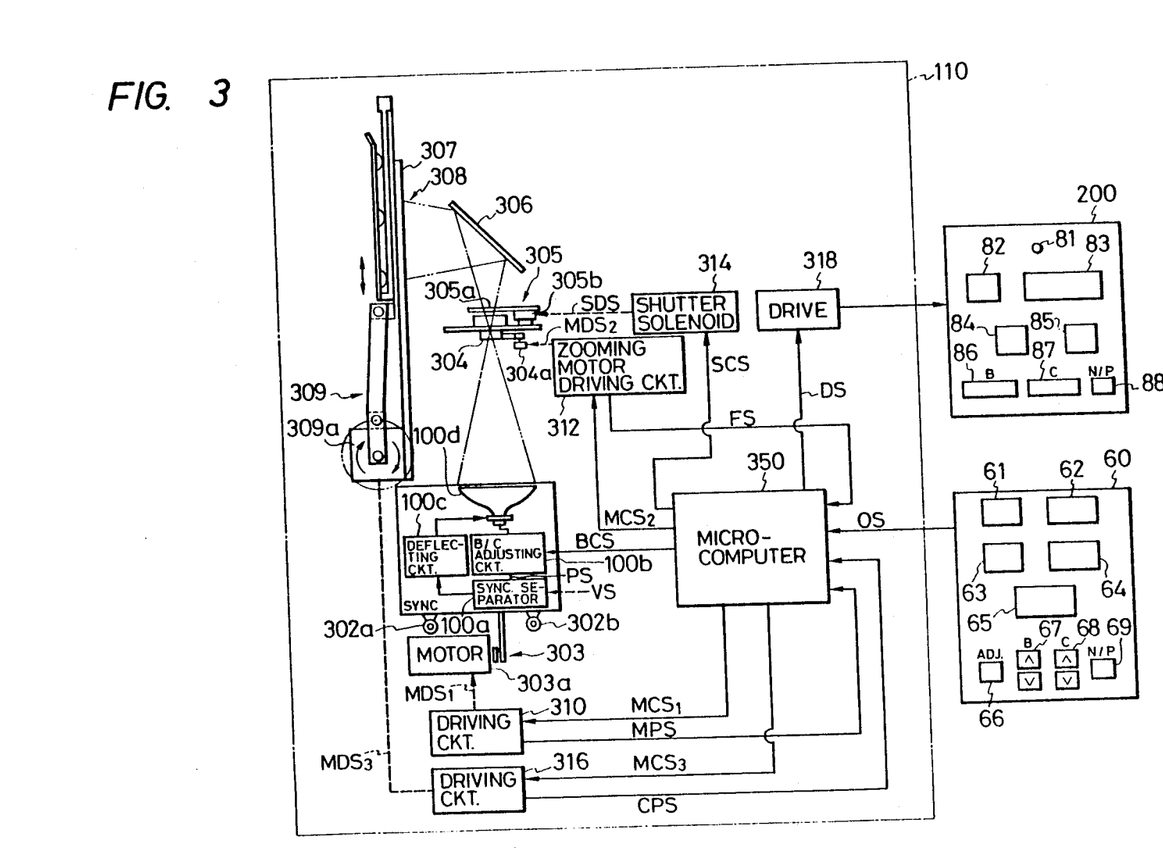
FIG. 3 is a schematic diagram of an image display device including a photographing control device.

FIG. 3 is a schematic diagram showing the displayed picture photographing device 110 and including the photography control device 270. In FIG. 3, the remote operation device 60 and the photography status indication device 200 are additionally shown (however, the photography status detection device 280 provided in association with the photography control device 270 is not illustrated).

An image pickup signal, which has been detected by the diagnostic image detection device 20, processed by the picture processing device 30, and converted into a video signal by the video signal converting circuit 40, is converted into an optical signal by the E/O converter 50 and transmitted to the O/E converter 90 through the optical cable 70. The optical signal is converted into an electrical signal again by the O/E converter 90, and then applied to the image display device 100 (for example, a television monitor) in which the electrical signal is separated by a synchronizing separator circuit 100a into a image signal PS and a synchronizing signal SYNC. The image signal PS is subjected to brightness and contrast adjustment, as well as to negative-to-positive conversion by a brightness/contrast adjusting circuit 100b controlled by a brightness/contrast control signal BCS from a microcomputer 350 (described below), and the electron beam of a cathode-ray tube (CRT) 100d is modulated accordingly. The synchronizing signal SYNC, on the other hand, is applied to a deflecting circuit 100c to control the deflection of the electron beam of the CRT 100d so that a diagnostic image is displayed on the screen of the CRT 100d. The monitor 100 is mounted so as to be horizontally movable on guides 302a and 302b and movable by a displacing mechanism 300 provided with a motor 303a. The motor 303a is driven by a motor driving signal $MDS_1$ from a monitor displacing motor driving circuit 310 conrolled by a monitor displacing motor control signal signal $MCS_1$ from the microcomputer 350.

The image displayed on the CRT 100d of the monitor 100 is focused onto a photo-sensitive material accommodated in a cassette 307 through a photographing zoom lens 304, shutter device 305, and a mirror 306 which are integrally displaced together with the television monitor. The zoom lens 304 is arranged such that the focal length thereof can be adjusted so as to change the scale factor by operation of a motor 304a driven by a signal $MDS_2$ from a zoom motor driving circuit 312, which is in turn controlled by a zoom motor control signal $MCS_2$ from the microcomputer 350. Further, a photographic shutter 305a is driven to be opened/closed by a rotary solenoid 305b, that is, the shutter is driven by a solenoid driving signal SDS from a shutter actuating solenoid driving circuit 314, which is in turn controlled by a shutter actuating solenoid control signal SCS from the microcomputer 350. The cassette 307 is held by a cassette holding portion 308 which is vertically displaceable by a cassette displacing mechanism 309 provided with a motor 309a. This motor 309a is driven by a motor driving signal $MDS_3$ from a cassette displacing motor driving circuit 316 controlled by a cassette displacing motor control signal $MCS_3$ from the microcomputer 350.

As described above, the television monitor 100 and the cassette 307 are displaced to change the focal length of the zoom lens 304 to thereby make it possible to record a plurality of images on one sheet of photosensitive material.

An operation signal OS produced by the remote operation device 60, a television monitor positioning signal MPS from the television monitor displacing motor driving circuit 310, a cassette positioning signal CPS from the cassette displacing motor driving circuit 316, and a scale factor signal FS from the zoom driving circuit 312 are applied to the microcomputer 350 to cause it to instruct predetermined operations on the basis of these signals so that various kinds of control signals, such as the brightness/contrast control signal BCS, the television monitor displacing motor control signal $MCS_1$, the zoom motor control signal $MCS_2$, the cassette displacing motor control signal $MCS_3$, and the shutter actuating solenoid control signal SCS are produced and, at the same time, a display signal DS is also produced to perform various kinds of display operations.

In the remote operation device 60, there are provided a photography preparation switch 61 for performing, for example, loading of a film cassette or a power switch, a photography switch 62 for performing exposure, a frame number setting switch 63 for selecting the number of frames to be recorded on the sheet of film, a photographic order setting switch 64 for selecting the order to be recorded on one sheet of film, and a photography condition setting switch 65 for selecting a photography condition channel which is suitable for the given photographic characteristics, the type of film, etc., among the plurality of set photographing condition channels, There are further provided an adjusting switch 66 which is turned "ON" to perform adjustment of the brightness and contrast, etc., a brightness adjusting switch 67 for setting the brightness, a contract adjusting switch 68 for setting the contrast, and a negative/positive reversing switch 69 for selecting the status of the displayed image on the CRT 100d between a positive and a negative mode. In the photography status indication device, there are provided an abnormal state indication lamp 81, an indicator unit 82 for indicating a selected photography condition channel, an indicator unit 83 for indicting a set photographic format (the number of photographic frames, the photographing order, etc.), an indicator unit 84 for indicating the number of available photographic films, an indicator unit 85 for indicating the number of photographic frames, a brightness value indicator unit 86, a contrast value indicator unit 87, and a negative/positive indicator unit 88.

Although the remote operation device 60 and the photographing status indication device 200 are provided separately from each other in FIG. 3, the arrangement may be modified such that these devices are integrated with each other so as to be constructed as a single unit.

Figure 4:
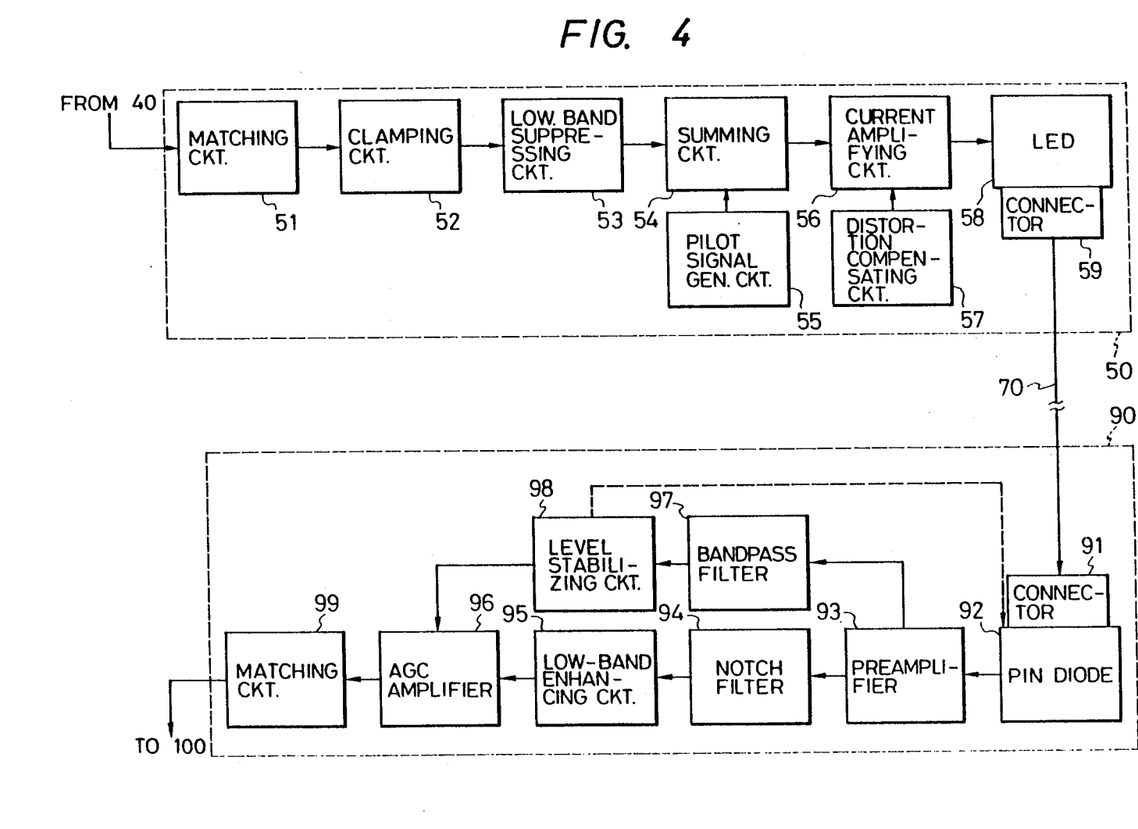
FIG. 4 is a block diagram of E/O and O/E converters used in the system according to the present invention.

Referring to FIG. 4, the E/O converter 50 and the O/E converter 90 will be described. The E/O and O/E converters are improved converters for properly converting high-frequency signals of an image of 1000 or more scanning lines per screen both electro-optically and opto-electrically, and which have improved frequency and phase characteristics.

An input video signal transferred from the video signal converting circuit 40 is terminated with the line impedance by a matching circuit 51, and the DC level of the video signal is clamped by a clamping circuit 52 so that the video signal will have levels which fall within the range of good linearity of a light-emitting device (LED) (described below). Further, it is possible to suppress the low frequency components of the video signal using a low-band suppressing circuit 53 to reduce the load of the LED and to reduce low frequency "sagging" due to heat, which is peculiar to an LED. In such a case, the output signal of the low band suppressing circuit 53 is summed with the output signal of a pilot signal generating circuit 55 by a summing circuit 54. The output signal of the summing circuit 54 is amplified by a current amplifying circuit 56 in accordance with the characteristic of a distortion compensating circuit 57. The distortion compensating circuit 57 has a characteristic determined so as to improve the distortion of the input video signal due to the nonlinearity of an LED in accordance with an appropriate distortion compensating characteristic (DG compensation or DP compensation). The output signal of the current amplifying circuit 56 is applied to a light-emitting device 58, which is in turn connected to the optical fiber cable 70 through a connector 59.

The input of the O/E converter 90 is connected to the optical fiber 70 through a connector 91. The input optical signal is thus converted to an electrical signal by a light-detecting device (e.g., PIN photo diode) 92. The resulting electrical signal is converted by a preamplifier 93 from a current signal into a voltage signal, which is in turn applied to a low band enhancing circuit 95 after unwanted frequency components have been removed therefrom by a notch filter 94, when a low band suppressing circuit is used on the transmitter side. In the low band enhancing circuit 95, the low band components of the above-mentioned voltage signal are amplified to a predetermined level so that a signal having the same frequency spectrum as the original signal applied to the E/O converter is regenerated. The thus-recovered signal is applied to an AGC amplifier 96 to which the pilot signal, subtracted from the preamplifier 93 by a band-pass filter 97, is also applied through a level stabilizing circuit 98. A video signal having a stabilized output voltage is reproduced at the output of the AGC amplifier 96. This video signal is applied to a video signal input terminal of the image display device 100.

The optical fiber cable used in the present invention will be described.

The optical fiber cable 70 is preferably made of a material in which Rayleigh scattering, absorption due to impurities, infrared absorption, and loss are particularly low, and which is suitable in the case where an LED and a PIN photo diode are used as the light-emitting device and the light-detecting device, respectively.

An optical fiber cable thus-manufactured was compared with conventional high-frequency cables, and the results described in the table below were obtained.

|  | Attenuation characteristics | | |
| --- | --- | --- | --- |
|  | 1 MHz | 10 MHz | 40 MHz (dB/km) |
| 3C2V (75 ohms) | 12 | 32–42 | 80 |
| 5C2V (75 ohms) | 8 | 27 | 50 |
| Optical Fiber | 2–4 | 2–4 | 2–4 |

In order to corroborate these characteristics, a video signal containing a large number of scanning lines, such as 1084/60 Hz, was transmitted through E/O and O/E converters connected at the opposite ends of each of the cables listed above. Each cable had a length of 1 km. It was found that no attenuation in the high frequency band an no variation in phase characteristics could be measured in the cable according to the present invention, and hence the image at the transmitter side could be faithfully reproduced at the receiver side.

If two optical fiber cables of the type described above are separately additionally provided and one of these optical fiber cables is used to connect the E/O converter 220 of the remote operation device 60 to the O/E converter 250 of the photographing control device 270 of the displayed image photographing device 110, and the another optical fiber cable is connected to the E/O converter 260 of the photography status detecting device 280 of the displayed image photography status indication device 200, it is possible to faithfully transmit both a picture signal and a control signal and a status indication signal.

Further, if a bidirectional composite optical fiber cable is used in place of the separate pair of optical fiber cables, the control signal and the status indication signal can be transmitted through the single optical fiber cable.

Further, in the case of the use of an opto-metallic composite cable, it is possible to transmit the photography control signal from the remote operation unit to the displayed image photographing device through a conductive metal member of the opto-metallic composite cable.

Alternatively, it is possible to transmit the output signal of the photography status detecting device to the photography status indication device through the metal member of the opto-metallic composite cable described above.

Furthermore, in the case where the photographing control signal from the remote operation unit is transmitted to the displayed image photographing device through the conductive metal member of the opto-metallic composite cable described above, the photographing control signal may be an electric power source operating signal of the photographing control means.

As described above, the medical image diagnostic system of the present invention is applicable not only to a diagnostic image detecting means, but also to a diagnostic image storing means. In such a system, a signal stored in an image filing means such as an optical disc may be processed and transmitted for a display, and then stored in the image storing means.

In the case where the system is constructed by coupling a conventional image output device and an image display device, or a conventional image display device and a displayed image photographing device, according to the present invention, as described above, long distance transmission of an image, particularly in the case of an image defined by high density scanning lines, which has been so far impossible, is enabled by the use of an optical fiber cable. In the case where a diagnostic image obtained by the diagnostic image detecting device is transmitted over a long distance to display it at the terminal, it is possible to display a picture of high quality, and also in the case of photographing the displayed image, it is possible to obtain a recorded picture of high quality.

Moreover, the following effects are obtained in the case where various kinds of cables are used as transmission lines.

(1) In the case where an analog video signal is transmitted via an optical fiber cable and a digital control signal is transmitted using a separately provided metal cable:

(a) It is possible to remotely operate the photographing control device. That is, it is possible to perform photography while controlling the image displayed on the image display device.

(b) If the photography status indication device is provided on the console side, it is possible to perform photography more surely so as to reduce the number of photography failures.

(c) If a remote power source control line is provided, it is possible to turn the photographing device ON according to demand so as to increase safety, energy savings, and power savings.

If an opto-metallic composite fiber cable is used as the optical fiber cable described above:

(d) It is possible to simplify the installation of the system to ensure its reliability, and to reduce the cost of the transmission lines.

(2) In the case where an opto-metallic composite fiber cable having a plurality of optical fiber cables is used and an analog video signal is transmitted via one optical fiber cable and digital control (display) signals of the remote control device and the photography status indication device are transmitted via other sets of optical fiber cables;

(a) It is possible to shield out external electromagnetic radiation so as to ensure reliability in transmission.

(b) There occurs no electromagnetic interference or crosstalk so that, even in the case where other important signal transmission lines are included in the opto-metallic composite fiber cable, such signal lines will not be affected.

(c) Since all of the signal transmission lines are constituted by optical fibers, it is possible to easily lay the transmission lines because of their compactness, light weight and flexibility, and the safety of the lines is ensured because of the insulating properties thereof. Further, it is possible to realize higher transmission speeds, a greater capacity, a wider frequency bandwidth, a lower loss, and smaller energy consumption.

(d) In the case where power source remote-control lines are provided, it is possible to obtain on/off control of the power source of the photographing device, the E/O, or O/E through a remote operation according to demand, and it is possible to thereby increase the lifetime of each of the light-emmiting element and light-detecting element of each of the E/O and O/E.

(3) In the case where a single bidirectional optical fiber is used in place of a plurality of digital signal transmitting cables, it is possible to make the transmission line low in cost and compact in size.

Thus, according to the present invention, it is possible to construct a superior system which is high in reliability as well as in safety, which is superior in operating properties, which is compact and inexpensive, and which is capable of transmitting images of high quality.

I claim:

1. A medical image diagnostic system, comprising;
   diagnostic image detecting means;
   image processing means receiving an output signal from said diagnostic image detecting means;
   video signal converting means receiving an outut signal of said image processing means and converting said signal to a video signal;
   electro-optic converting circuit means receiving an output of said video signal converting means and converting said signal to an optical signal;
   opto-electric converting circuit means for receiving said optical signal and for converting said signal into an electrical signal;
   optical cable means coupling said electro-optic and opto-electric converting circuit means;
   image display means driven by an output signal of said opto-electric converting circuit means;
   photographing means located proximate said image display means for photographing images displayed on said image display means, and photographic control means for controlling the operation of said photographing means in response to a control signal;
   remote operating means for remotely controlling said photographing means and for generating said control signal;
   photographic status detection means for detecting the status of said photographing means and for generating a status output signal, said status detection means being located at said photographing means; and
   status indicator means located in the vicinity of said remote operating means and being controlled by said status detection means.

2. The medical image diagnostic system according to claim 1, wherein said electro-optic converting circuit means comprises means for directly intensity-modulating an output signal based upon an input analog video signal.

3. The medical image diagnostic system according to claim 1, wherein said remote operating means and said status indicator means are provided in the form of an integrated unit.

4. The medical image diagnostic system according to claim 1, wherein said status output signal from said photographic status detection means is transmitted by a metal member of an opto-metallic composite cable.

5. The medical image diagnostic system according to claim 1, wherein said electro-optic converting circuit means comprises a plurality of sets of electro-optic converting circuits and wherein said opto-electric converting circuit means comprises a plurality of sets of opto-electric converting circuits, a first one of said electro-optic converting circuits and a corresponding first one of said opto-electric converting circuits transmitting said control signal from said remote operating means to said photographic control means through said optical cable means, and a second one of said electro-optic converting circuits and a corresponding second one of opto-electric converting circuits transmitting a digital signal from said photographic status detection means to said status indicator means through said optial cable means.

6. The medical image diagnostic system according to claim 5, wherein an electric power source of said photographic control means is operated by said remote operating means through a metal member of an opto-metallic composite cable.

7. The medical image diagnostic system according to claim 5, wherein said first one of said electro-optic converting circuits and said first one of said opto-electric converting circuits are coupled through a bidirectional transmission optical fiber cable.

8. The medical image diagnostic system according to claim 7, wherein an electric power source of said photographic control means is operated by said remote operating means through a metal member of an opto-metallic composite cable.

9. The medical image diagnostic system according to claim 8, wherein said diagnostic image detecting means comprises diagnostic image storing means.

10. The medical image diagnostic system according to claim 5, wherein said control signal from said remote operating means is transmitted by a metallic member of an opto-metallic composite cable.

11. The medical image diagnostic system according to claim 10, wherein said control signal transmitted by said metallic member of said composite cable includes a control signal for on/off controlling an electric power source of said photographic control means.

12. A medical image diagnostic system, comprising;
diagnostic image detecting means;
image processing means receiving an output signal from said diagnostic image detecting means;
video signal converting means receiving an output signal of said image processing means and converting said signal to a video signal;
electro-optic converting circuit means for receiving an output of said video signal converting means and for converting said signal to an optical signal, said electro-optic converting circuit means comprising a plurality of sets of electro-optic converting circuits;
opto-electric converting circuit means for receiving said optical signal and for convertng said signal into an electrical signal, said opto-electric converting circuit means comprising a plurality of sets of opto-electric converting circuits;
optical fiber cable means coupling said electro-optic and opto-electric converting circuit means;
image display means driven by an output signal of said opto-electric converting circuit means;
means for photographing images displayed on said image display means;
means for controlling the operation of said photographing means in response to a control signal;
remote operating means for remotely controlling said photographing means and for generating said control signal;
a first one of said electro-optic converting circuits and a corresponding first one of said opto-electric converting circuits transmitting said control signal from said remote operating means to said control means through said optical fiber cable means;
status detection means for detecting the status of said photographing means;
status indicator means controlled by said status detection means; and
a second one of said electro-optic converting circuits and a corresponding second one of said opto-electric converting circuits transmitting a digital signal from said photographic status detection means to said status indicator means through said optical fiber cable means.

13. A medical image diagnostic system, comprising;
diagnostic image detecting means;
image processing means receiving an output signal from said diagnostic image detecting means;
video signal converting means receiving an output signal of said image processing means and converting said signal to a video signal;
electro-optic converting circuit means receiving an output of said video signal converting means and converting said signal to an optical signal;
opto-electric converting circuit means for receiving said optical signal and for converting said signal into an electrical signal;
an opto-metallic composite cable coupling said electro-optic and opto-electric converting circuit means;
image display means driven by an output signal of said opto-electric converting circuit means;
photographing means located proximate said image display means for photographing images displayed on said image display means, and photographic control means for controlling the operation of said photographing means in response to a control signal;
remote operating means for remotely controlling said photographing means and for generating said control signal;
photographic status detection means for detecting the status of said photographing means and for generating a status output signal, said status detection means being located at said photographing means;
status indicator means located in the vicinity of said remote operating means and being controlled by said status detection means; and
at least said control signal from said remote operating means being transmitted by a metallic member of said opto-metallic composite cable.

* * * * *